US006632179B2

(12) United States Patent
Wilson et al.

(10) Patent No.: US 6,632,179 B2
(45) Date of Patent: Oct. 14, 2003

(54) ACOUSTIC IMAGING SYSTEM WITH NON-FOCUSING LENS

(75) Inventors: Martha Grewe Wilson, Andover, MA (US); Wojtek Sudol, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 50 days.

(21) Appl. No.: 09/919,122

(22) Filed: Jul. 31, 2001

(65) Prior Publication Data

US 2003/0028104 A1 Feb. 6, 2003

(51) Int. Cl.[7] .................................................. A61B 8/00
(52) U.S. Cl. ........................................................ 600/460
(58) Field of Search ................................ 600/437, 460, 600/459, 461, 458, 443

(56) References Cited

U.S. PATENT DOCUMENTS

| | | | | |
|---|---|---|---|---|
| 5,671,746 A | * | 9/1997 | Dreschel et al. | 600/459 |
| 5,792,058 A | | 8/1998 | Lee et al. | 600/459 |
| 6,095,978 A | * | 8/2000 | Takeuchi | 29/25.35 |
| 6,171,248 B1 | * | 1/2001 | Hossack et al. | 600/447 |
| 6,194,814 B1 | | 2/2001 | Hanafy et al. | 310/334 |

* cited by examiner

*Primary Examiner*—Francis J. Jaworski
*Assistant Examiner*—Maulin Patel
(74) *Attorney, Agent, or Firm*—John Vodopia

(57) ABSTRACT

Acoustic imaging systems are provided. A preferred system includes a transducer lens configured to mate with a transducer body. The transducer lens is configured to propagate acoustic energy. Preferably, the transducer lens is formed, at least partially, of an acoustic-matching material, which exhibits acoustic properties corresponding to acoustic properties of a body to be imaged. Methods also are provided.

20 Claims, 7 Drawing Sheets

ACOUSTIC IMAGING SYSTEM WITH NON-FOCUSING LENS

BACKGROUND OF THE INVENTION

1. Field of the Invention

The present invention generally relates to acoustic imaging and, more specifically, to ultrasonic imaging systems and methods that utilize acoustically non-focusing lenses.

2. Description of the Related Art

Conventional one-dimensional (1-D) phased array transducers utilized for ultrasonic imaging typically incorporate lenses that focus acoustic beams transmitted from the transducers. In particular, the material properties of such a lens typically are selected to focus an acoustic beam from a transducer in an elevational dimension. The elevational dimension also may be focused mechanically, such as by implementing a concave shape at the array of the transducer. The lateral dimension typically is focused electronically.

By way of example, a conventional 1-D phased array transducer utilizes a lens that promotes focusing of transmitted acoustic energy within a body, e.g., a human body. Oftentimes, the material of such a lens possesses an acoustic velocity that is less than that of the human body (approximately 1.5 mm/$\mu$sec). So provided, the acoustic energy propagated into the body by the lens tends to converge or focus within the body. Focusing of acoustic energy transmitted from a conventional 1-D transducer within a body is depicted schematically in FIG. 1.

In FIG. 1, representative acoustic waves 12, 14, 16, 18, and 20 are shown being transmitted from transducer 22 via focusing lens 24. As depicted therein, the acoustic waves tend to focus as they propagate deeper into body 30 due, at least in part, to the material of the lens.

As is known, acoustic energy propagates at various velocities and with various wave-front shapes depending upon, for example, the acoustic velocity and acoustic impedance of a material(s) through which the acoustic energy is propagated. For instance, the closer the acoustic velocity of a lens material is to that of the body, the closer the energy is transmitted from a transducer and into the body at the incident angle. Additionally, the closer the acoustic impedance is between the lens material and that of the body, the more ultrasonic energy is transmitted from the transducer and into the body.

Since it is known to electronically focus acoustic beams propagated from two-dimensional (2-D) transducers in both the elevational and lateral dimensions, there may no longer be a desire to mechanically focus acoustic beams propagated into a body to the degree typically provided. However, many 2-D transducers continue to utilize convex lenses, which tend to mechanically focus propagated acoustic energy. Therefore, there is a need for improved systems and methods that address these and/or other shortcomings of the prior art.

SUMMARY OF THE INVENTION

Briefly described, the present invention generally relates to acoustic imaging. In this regard, embodiments of the invention may be construed as providing acoustic imaging systems. In a preferred embodiment, the system includes a transducer lens configured to mate with a transducer body. The transducer lens is formed, at least partially, of an acoustic-matching material, which exhibits acoustic properties corresponding to acoustic properties of a body to be imaged. So configured, acoustic energy transmitted from the transducer lens and into the body can be substantially non-focusing until modified by electronic focusing techniques.

Other embodiments of the present invention may be construed as providing methods for acoustically imaging a patient, for example. A preferred method comprises the steps of: (1) providing a transducer having a transducer lens formed, at least partially, of an acoustic-matching material; and (2) propagating acoustic waves from the transducer lens.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF A PREFERRED EMBODIMENT

Figure 1:
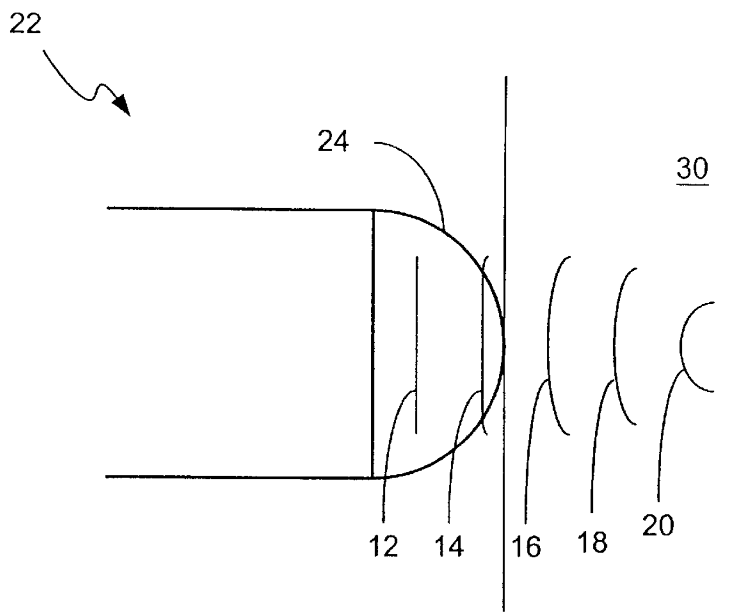
FIG. 1 (PRIOR ART)
FIG. 1 is a schematic diagram depicting a prior art transducer transmitting acoustic energy into a representative body.
Figure 2:
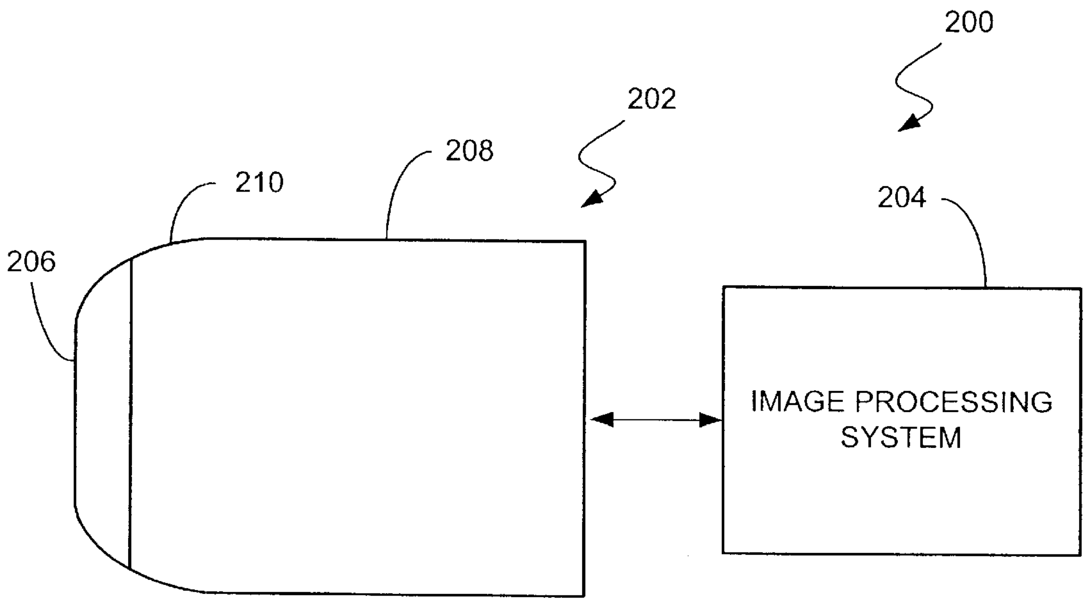
FIG. 2 is a schematic diagram depicting a preferred embodiment of the imaging system of the present invention.

As shown in FIG. 2, a preferred embodiment 200 of the imaging system of the present invention incorporates a transducer probe ("transducer") 202. By way of example, transducer 202 can be a two-dimensional (2-D) phased array transducer, although other configurations of transducers can be utilized. Transducer 202 electrically communicates with an image processing system 204. Image processing system 204 provides signals to transducer 202 so as to enable the transducer to transmit acoustic energy via lens 206. The transducer receives reflected acoustic energy via lens 206 and provides signals corresponding to the received acoustic energy to the image processing system for processing.

Lens 206 is maintained in position relative to the transducer body 208 by a nose 210 of the transducer body. In particular, lens 206 is adapted to seat at least partially within an aperture defined by the nose. Various other configurations, however, can be used.

Preferably, lens 206 is configured as an acoustically non-focusing lens. More specifically, lens 206 is formed of a selected material(s) and/or exhibits a particular shape that enables acoustic energy to be propagated into a body, e.g., a human body, without substantially mechanically focusing the acoustic energy. By way of example, embodiments of the invention may utilize a lens that is at least partially formed of an acoustic-matching material. Such an acoustic-matching material preferably exhibits an acoustic velocity and an acoustic impedance that substantially match the acoustic velocity and acoustic impedance of a typical body. For instance, a material exhibiting an acoustic velocity within the range of approximately 1.4 to approximately 1.6 mm/μsec could be considered an acoustic-matching material. An acoustic-matching material also preferably exhibits an acoustic impedance within the range of approximately 1.3 to approximately 1.7 MRayl.

In some embodiments, the acoustically non-focusing lens may be formed of butadiene, styrene butadiene, and/or an associated classes of rubbers and/or polymers, among others. These materials typically attenuate acoustic energy at approximately 3 db/cm at 2 MHz and approximately 8 db/cm at 5 MHz. As is known, conventional lens materials, such as silicone, attenuate acoustic energy at approximately 9 db/cm at 2 MHz and approximately 33 db/cm at 5 MHz.

It should be noted that one of ordinary skill in the art may choose to provide a lens formed of materials that, individually, may not be considered an acoustic-matching materials. However, providing a combination of materials that together exhibit acoustic-matching properties, e.g., an acoustic velocity within the range of approximately 1.4 to approximately 1.6 mm/μsec and an acoustic impedance within the range of approximately 1.3 to approximately 1.7 MRayl, is considered well within the scope of the invention.

By providing an acoustically non-focusing lens, imaging system 200 may enable transmission of acoustic energy into a body that is suitable for electronic focusing in both the lateral and elevational dimensions. In particular, the imaging system may provide acoustic beams that are conducive to comparatively sensitive electronic focusing. This could facilitate improved zoom imaging functionality as compared to other systems which use mechanically focusing lenses. It also is presumed that an imaging system using an acoustically non-focusing lens may provide acoustic beams that are particularly well suited for contrast imaging applications. As described in greater detail hereinafter, imaging systems of the invention can include various shapes of lenses, which are at least partially formed of acoustic-matching material.

Figure 3:
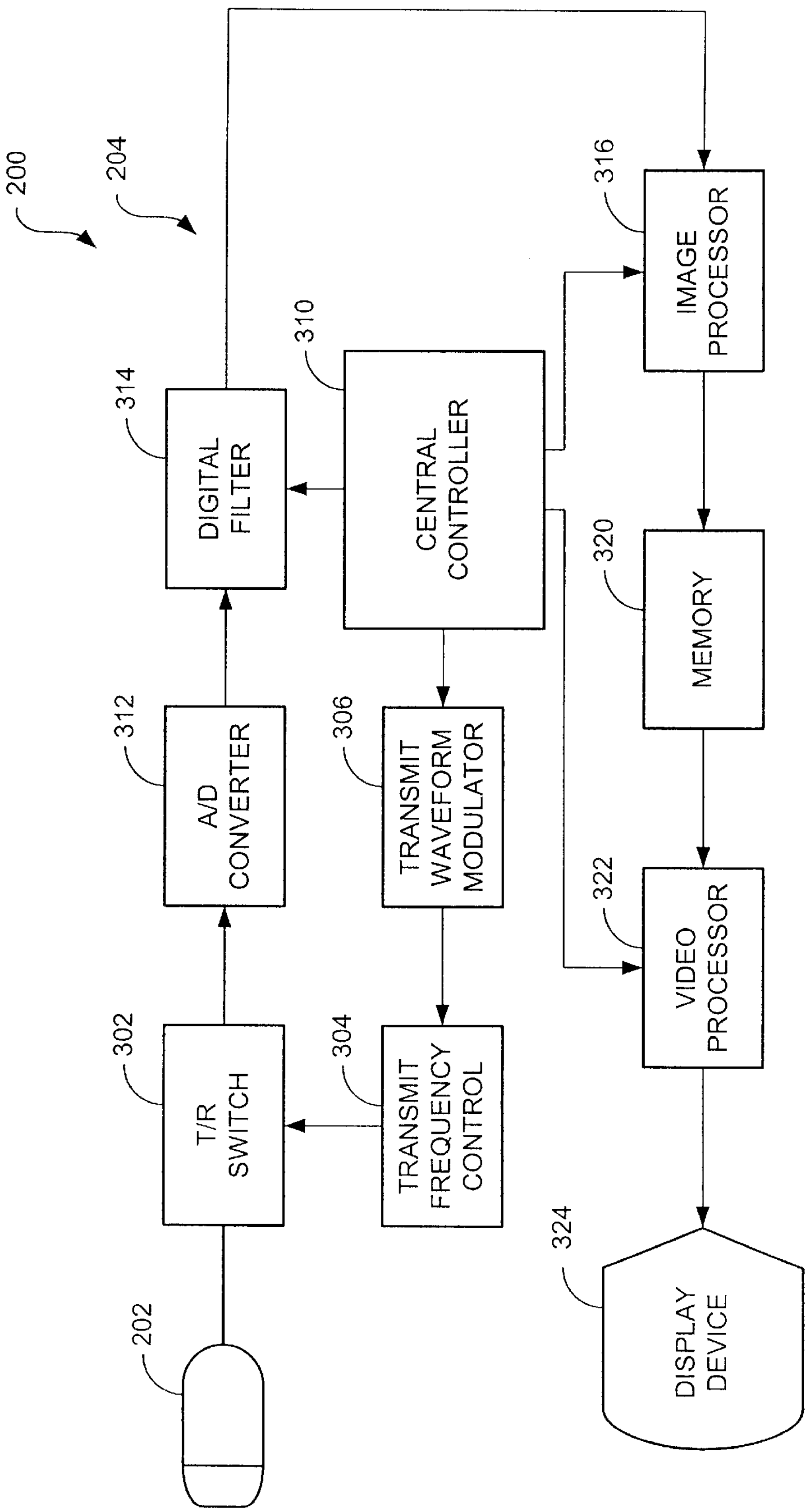
FIG. 3 is a schematic diagram of the embodiment of FIG. 2 showing detail of the image processing system.

Referring now to FIG. 3, a preferred embodiment of the imaging system 200 and, more specifically, image processing system 204, will be described in greater detail. It will be appreciated that FIG. 3 does not necessarily illustrate every component of the preferred system, emphasis instead being placed upon the components most relevant to the systems and/or methods disclosed herein.

As depicted in FIG. 3, imaging system 200 includes a transducer 202, which is electrically connected to a T/R switch 302 of image processing system 204. T/R switch 302 places the transducer in either a transmit or receive mode. In order to facilitate transmission of acoustic energy via the transducer during operation in the transmit mode, image processing system 204 includes a transmit frequency controller 304 that sets the transmit frequency $f_o$ of transmit signals and a transmit waveform modulator 306 that modulates the various transmitted signal lines. The transmit frequency controller 304 and transmit waveform modulator 306 operate under control of a central controller 310.

In order to facilitate reception of acoustic energy via the transducer during operation in the receive mode, image processing system 204 includes an A/D converter 312, which converts analog signals received from transducer 202 into digital signals. A digital filter 314, e.g., an RF filter, filters signals outside a desired receive band from the received data. An image processor 316 is provided for processing received data, with processed data then typically being provided to memory 320 for storage, as required. A video processor 322 also preferably is provided for enabling display of information corresponding to the received data on a display device 324.

Figure 4:
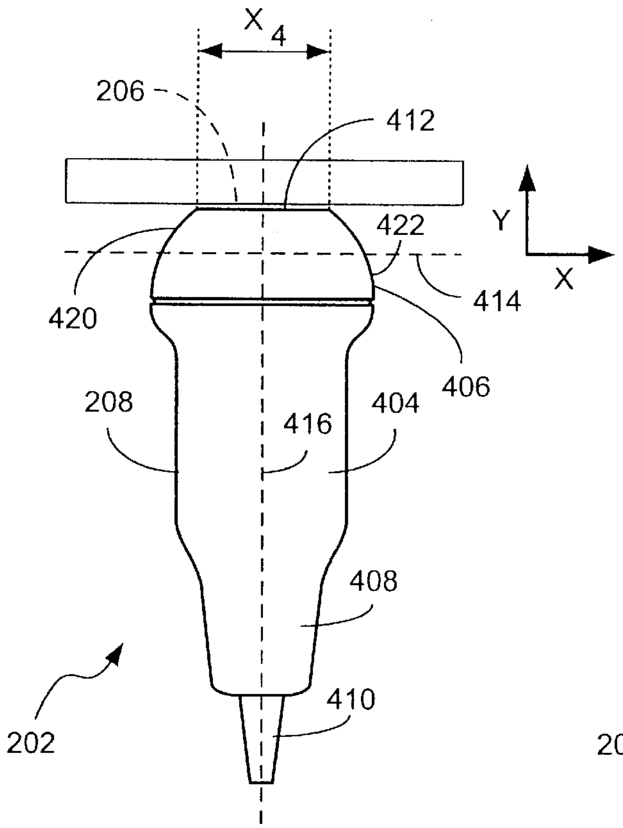
FIG. 4 is a plan view of a preferred embodiment of the transducer of the present invention shown in relation to a representative, schematically-depicted, rib.
Figure 5:
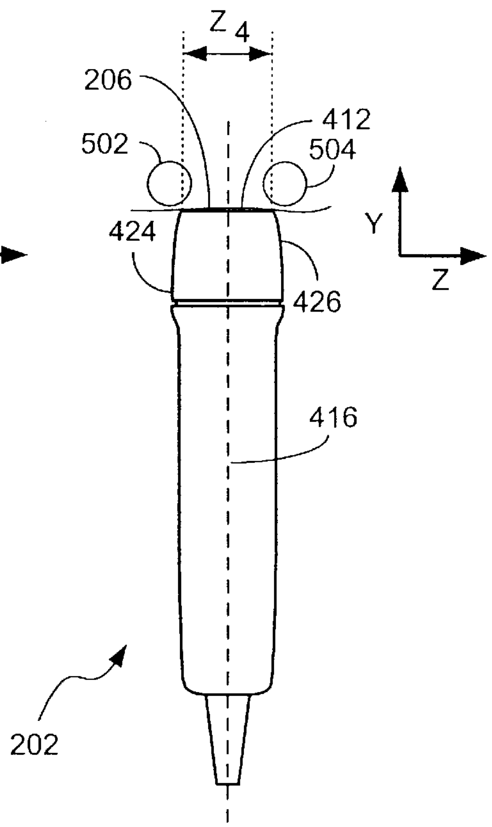
FIG. 5 is a side view of the embodiment of FIG. 4 showing representative positioning of the transducer in relation to representative, schematically-depicted, ribs.

Referring now to FIGS. 4 and 5, a preferred embodiment of transducer 202 will be described in greater detail. As depicted in FIG. 4, transducer 202 includes a body 402 and a lens 206. Body 402 preferably is configured so as to house one or more of various components required to facilitate transmission and/or reception of acoustic energy via lens 206. By way of example, such components may include an array of piezoelectric elements, among others. Body 402 also is configured to facilitate proper positioning of the transducer for performing an imaging procedure.

In the embodiment depicted in FIG. 4, body 402 includes an intermediate portion 404 that is appropriately adapted to be grasped by the hand of an operator. A lens-mounting portion 406, which preferably flares radially outwardly from intermediate portion 404, is adapted to engage lens 206. At the proximal end of body 402, i.e., the end opposite portion 406, a tapered or necked portion 408 is provided. Portion 408 defines an aperture for receiving electrical cordage 410. Cordage 410 is adapted to facilitate electrical communication between the transducer and image processing equipment (not shown).

Various shapes of lenses may be utilized. For instance, if a lens with a planar surface is used, the wave-fronts of acoustic energy propagated through the lens can be generally non-focusing. However, various considerations, such as the desire to promote good patient contact between the lens and the patient, for example, may make other shapes more desirable. For instance, in some embodiments, the lens can be physically configured so as to facilitate convenient alignment of the transducer with an acoustic window of a patient. In particular, such a lens preferably incorporates a planar tissue-engagement surface, with curved surfaces extending outwardly and rearwardly from the planar surface. This configuration tends to facilitate convenient positioning of the lens in relation to an acoustic window, such as an acoustic window defined by adjacent ribs of the patient. More specifically, the curved surfaces typically engage the ribs and tend to align the tissue-engagement surface with the acoustic window. As described hereinafter, the tissue-engagement surface may be provided in various configurations.

As shown in FIGS. 4 and 5, tissue-engagement surface 412 preferably is arranged substantially parallel to a transverse axis 414 of the transducer. So configured, this embodiment is enable to transmit acoustic energy from the transducer and propagate that energy along a path that is generally coextensive with a longitudinal axis 416 of the transducer. Preferably, a length $X_4$ of the tissue-engagement surface is selected so as to provide an appropriate cross-sectional area of engagement with a body so that an adequate amount of acoustic energy can be propagated from the transducer to the body.

A width $Z_4$ (FIG. 5) of tissue engagement surface 412 is selected so as to facilitate propagation of acoustic energy. However, the width also may be selected to exploit an appropriately selected acoustic window. More specifically, if lens 206 is to be utilized during a thoracic acoustic-imaging procedure, for example, width $Z_4$ may be selected so as to attempt to improve transducer positioning between adjacently disposed ribs, e.g., ribs 502 and 504, of the body to be imaged. So positioned, efficient propagation of acoustic energy from the transducer, between the ribs, and deeper into the body may be facilitated.

Surfaces 420, 422, 424 and 426 emanating from the tissue-engagement surface 412 generally are curved and smooth and can facilitate aligning of the tissue-engagement surface with an acoustic window. More specifically, when the tissue-engagement surface is appropriately sized, surfaces 424 and 426 tend to engage the ribs, e.g., ribs 502 and 504, thereby enabling the tissue-engagement surface to engage or nest between the ribs. Thus, the surfaces tend to align the tissue-engagement surface with the acoustic window. The curved surfaces also can enhance patient comfort during an imaging procedure as a non-curved surface may tend to cause localized discomfort.

Figure 6:
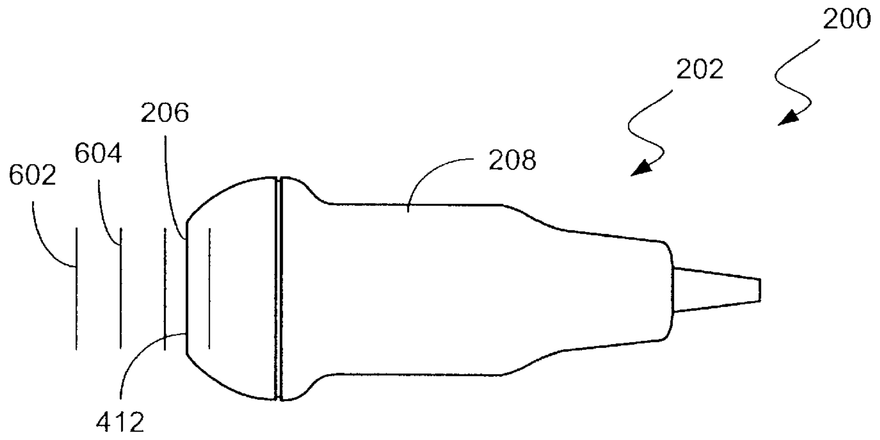
FIG. 6 is a schematic diagram of the embodiment of FIGS. 4 and 5 showing representative non-focused acoustic energy being transmitted through the non-focusing lens of the transducer.

Shown schematically in FIG. 6, utilization of the imaging system 200 and, more specifically, transducer 202 and corresponding lens 206, facilitates propagation of relatively non-focusing waves of acoustic energy, e.g., waves 602 and 604.

Figure 7:
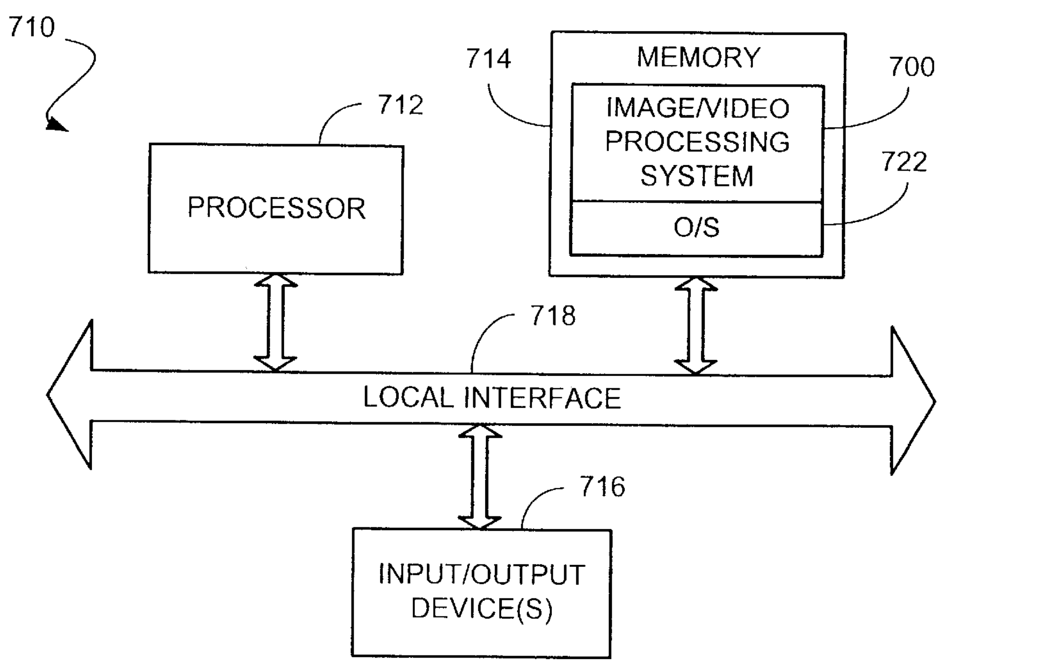
FIG. 7 is a schematic diagram depicting a computer or processor-based system that may be utilized to implement the imaging system of the present invention.

Referring once again to the image processing system 204 (FIG. 3), portions of that system may be implemented in software (e.g., firmware), hardware, or a combination thereof. In the embodiment depicted in FIG. 3, the central controller 310, image processor 316 and/or video processor 322, among others, may implemented in software, as executable programs, and are executed by a special or general purpose digital computer, such as a personal computer (PC; IBM-compatible, Apple-compatible, or otherwise), workstation, minicomputer, or mainframe computer. An example of a general purpose computer that can implement the image processor 316 and video processor 322 of the image processing system of the present invention is shown in FIG. 7. As utilized hereinafter, the functionality provided by the central controller 310, image processor 316 and video processor 322 is collectively referred to as the image/video processing system.

Generally, in terms of hardware architecture, as shown in FIG. 7, computer 710 includes a processor 712, memory 714, and one or more input and/or output (I/O) devices 716 (or peripherals) that are communicatively coupled via a local interface 718. The local interface 718 can be, for example but not limited to, one or more buses or other wired or wireless connections, as is known in the art. The local interface 718 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 712 is a hardware device for executing software that can be stored in memory 714. The processor 712 can be any custom made or commercially available processor, a central processing unit (CPU) or an auxiliary processor among several processors associated with the computer 710, and a semiconductor based microprocessor (in the form of a microchip) or a macroprocessor. Examples of suitable commercially available microprocessors are as follows: an 80x86 or Pentium series microprocessor from Intel Corporation, U.S.A., a PowerPC microprocessor from IBM, U.S.A., a Sparc microprocessor from Sun Microsystems, Inc, a PA-RISC series microprocessor from Hewlett-Packard Company, U.S.A., or a 68xxx series microprocessor from Motorola Corporation, U.S.A.

The memory 714 can include any one or combination of volatile memory elements (e.g., random access memory (RAM, such as DRAM, SRAM, etc.)) and nonvolatile memory elements (e.g., ROM, hard drive, tape, CDROM, etc.). Moreover, the memory 714 may incorporate electronic, magnetic, optical, and/or other types of storage media. Note that the memory 714 can have a distributed architecture, where various components are situated remote from one another, but can be accessed by the processor 712.

The software in memory 714 may include one or more separate programs, each of which comprises an ordered listing of executable instructions for implementing logical functions. In the example of FIG. 7, the software in the memory 714 includes the image/video processing system and a suitable operating system (O/S) 722. A nonexhaustive list of examples of suitable commercially available operating systems 722 is as follows: a Windows operating system from Microsoft Corporation, U.S.A., a Netware operating system available from Novell, Inc., U.S.A., or a UNIX operating system, which is available for purchase from many vendors, such as Sun Microsystems, Inc., Hewlett-Packard Company, U.S.A., and AT&T Corporation, U.S.A. The operating system 722 essentially controls the execution of other computer programs, such as the image/video processing system 700, and provides scheduling, input-output control, file and data management, memory management, and communication control and related services.

The image/video processing system 700 is a source program, executable program (object code), script, or any other entity comprising a set of instructions to be performed. When a source program, then the program needs to be translated via a compiler, assembler, interpreter, or the like, which may or may not be included within the memory 714, so as to operate properly in connection with the O/S 722. Furthermore, the image/video processing system 700 can be written as (a) an object oriented programming language, which has classes of data and methods, or (b) a procedure programming language, which has routines, subroutines, and/or functions, for example but not limited to, C, C++, Pascal, Basic, Fortran, Cobol, Perl, Java, and Ada.

The I/O devices 716 may include input devices, for example but not limited to, a keyboard, mouse, A/D converter, filter, etc. Furthermore, the I/O devices 716 may also include output devices, for example but not limited to, waveform modulator, a printer, display, etc. Finally, the I/O devices 716 may further include devices that communicate both inputs and outputs, for instance but not limited to, a transducer, T/R switch, modulator/demodulator (modem; for accessing another device, system, or network), a radio frequency (RF) or other transceiver, a telephonic interface, a bridge, a router, etc.

If the computer 710 is a PC, workstation, or the like, the software in the memory 714 may further include a basic input output system (BIOS) (omitted for simplicity). The BIOS is a set of essential software routines that initialize and test hardware at startup, start the O/S 722, and support the transfer of data among the hardware devices. The BIOS is stored in ROM so that the BIOS can be executed when the computer 710 is activated.

When the computer 710 is in operation, the processor 712 is configured to execute software stored within the memory 714, to communicate data to and from the memory 714, and to generally control operations of the computer pursuant to the software. The image/video processing system 700 and the O/S 722, in whole or in part, but typically the latter, are read by the processor 712, perhaps buffered within the processor 712, and then executed.

When the image/video processing system 700 is implemented in software, as is shown in FIG. 7, it should be noted that the image/video processing system 700 can be stored on any computer readable medium for use by or in connection with any computer related system or method. In the context of this document, a computer readable medium is an electronic, magnetic, optical, or other physical device or means that can contain or store a computer program for use by or in connection with a computer related system or method. The image/video processing system 700 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device.

The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

In an alternative embodiment, where the image/video processing system 700 is implemented in hardware, the image/video processing system 700 can implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 8:
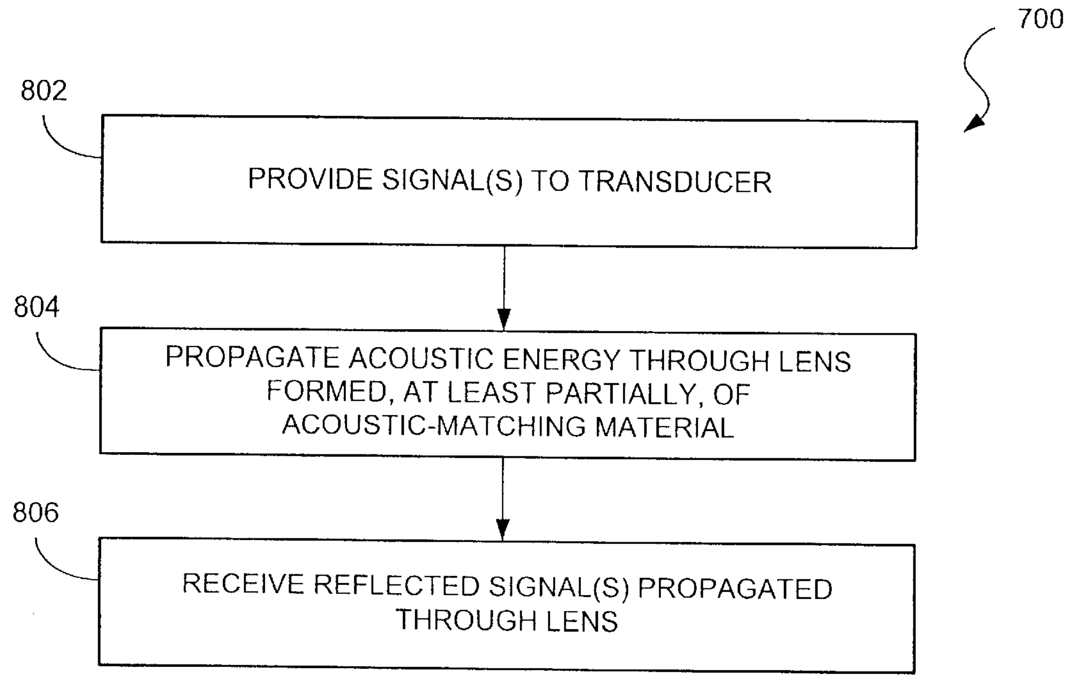
FIG. 8 is a flowchart depicting preferred functionality of the imaging system of FIG. 7.

As depicted in FIG. 8, the image/video processing system 700 or method may be construed as beginning at block 802 where an appropriate signal(s) is provided to the transducer. In block 804, acoustic energy is propagated through the lens, of the transducer, which is configured as an acoustically non-focusing lens. In these embodiments, the acoustic energy can be focused in the lateral and elevational dimensions. Thereafter, such as depicted in block 806, a reflected signal(s) propagated through the acoustically non-focusing lens is received.

Operation

Figure 9:
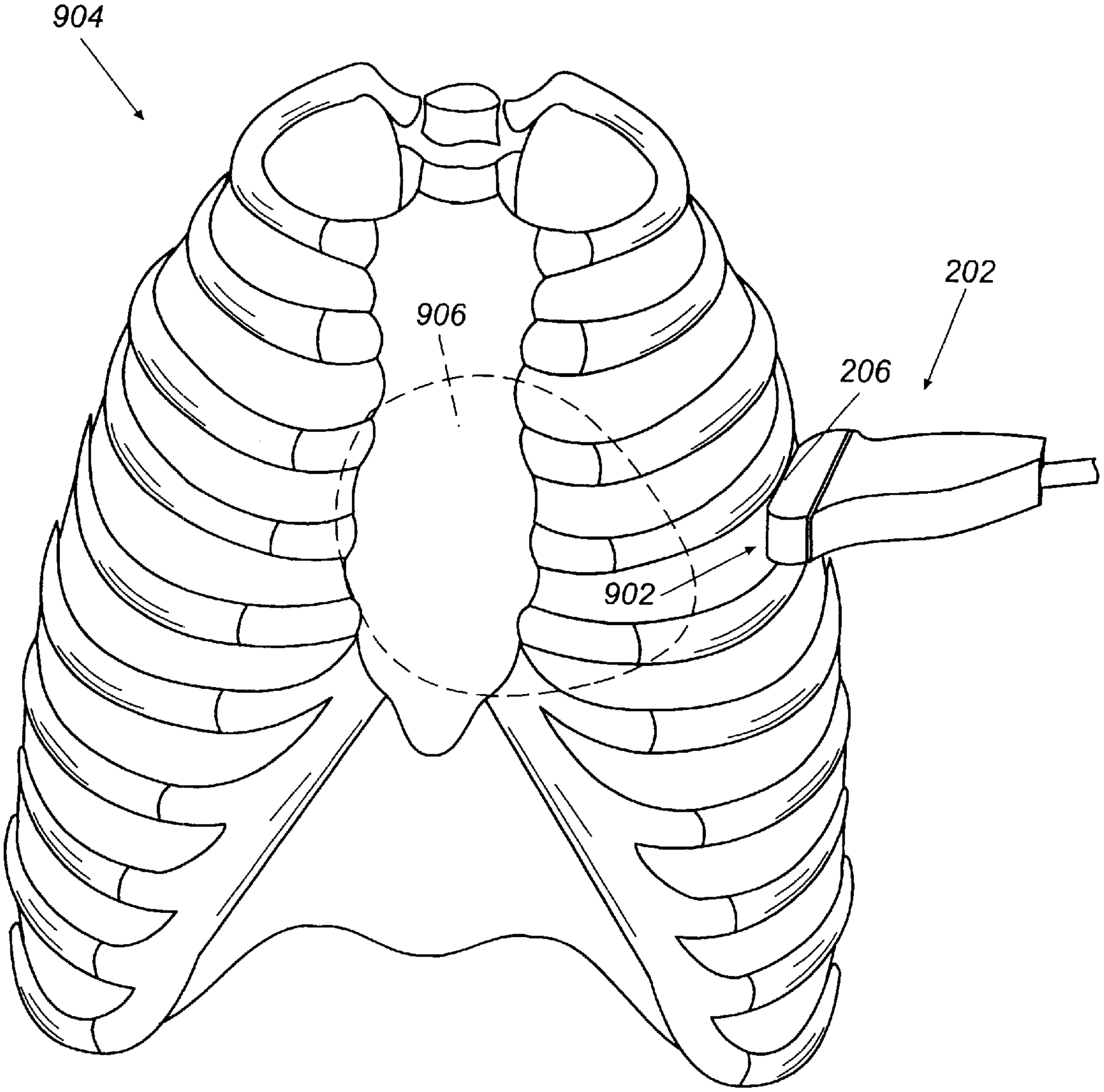
FIG. 9 is a schematic diagram depicting representative placement of the transducer of FIGS. 4 and 5 during a representative thoracic imaging procedure.

As depicted in FIG. 9, a preferred embodiment of the transducer 202 of the present invention is shown in operative engagement with a representative acoustic window. By way of example, the transducer is appropriately positioned at an acoustic window 902 or rib access point of a representative thoracic section 904 so as to enable acoustic imaging of a heart 906, for example. As may be seen in FIG. 9, rib access points tend to be geometry-limited structures, i.e., the rib access points provide a bounded area through which acoustic energy may be propagated (acoustic energy is unable to penetrate bone so as to be useful for imaging). Due to the shape of lens 206, the ability to exploit rib access points to provide acoustic imaging of tissues within the bony thorax is potentially increased. Moreover, the material(s) of the lens, possessing acoustic velocity and impedance much like that of the body, tends to enhance the amount of acoustic energy propagated through a rib access point. As mentioned hereinbefore, the acoustic energy can be electronically focused in both the lateral and elevational dimensions.

Figure 10:
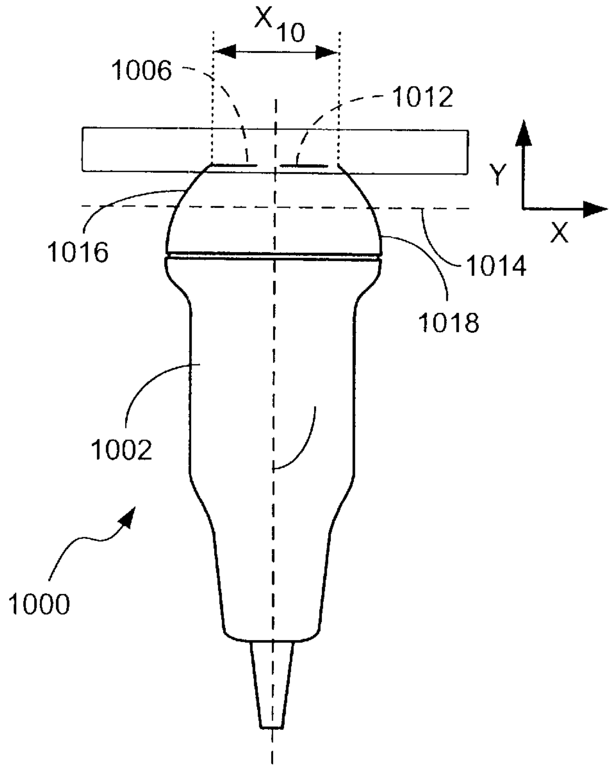
FIG. 10 is a plan view of an alternative embodiment of the present invention.
Figure 11:
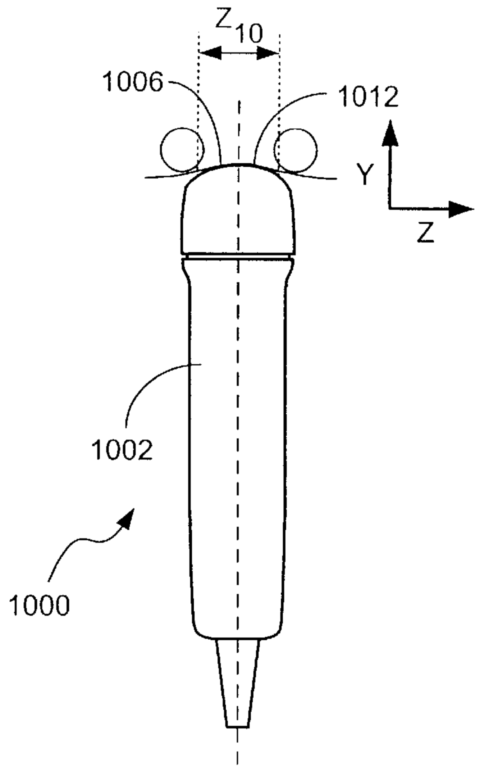
FIG. 11 is a side view of the embodiment of FIG. 10.

Referring now to FIGS. 10 and 11, an alternative embodiment of the imaging system will be described in greater detail. As depicted in FIG. 10, transducer 1002 includes a body 1002 and a lens 1006. Lens 1006 is configured as an acoustically non-focusing lens. Lens 1006 is configured, such as by being formed of a selected material(s) and/or possessing a particular shape to propagate acoustic energy into a body, e.g., a human body, so that the acoustic energy does not tend to substantially focus within the body unless electronically focused. Lens 1006 preferably is formed, at least partially, of an acoustic-matching material. Preferably, lens 1006 incorporates a generally cylindrical tissue-engagement surface 1012, e.g., the tissue-engagement surface generally is formed as a portion of a cylinder. Tissue-engagement surface 1012 preferably is arranged substantially parallel to a transverse axis 1014 of the transducer and is provided so as to enable acoustic energy transmitted from the transducer to propagate along a path that is generally coextensive with a longitudinal axis 1016 of the transducer.

Preferably, a length $X_{10}$ of the tissue-engagement surface is selected so as to provide an appropriate cross-sectional area of engagement for propagating acoustic energy from the transducer to a body. As depicted in FIG. 11, a width $Z_{10}$ of tissue engagement surface 1012 also is selected so as to facilitate propagation of acoustic energy; however, the width also may be selected to exploit an appropriately selected acoustic window. Surfaces 1016 and 1018 emanating from the tissue-engagement surface 1012 generally are curved and smooth surfaces that extend outwardly and rearwardly toward the transducer body so as to form a portion of a sphere (when viewed in plan).

Figure 12:
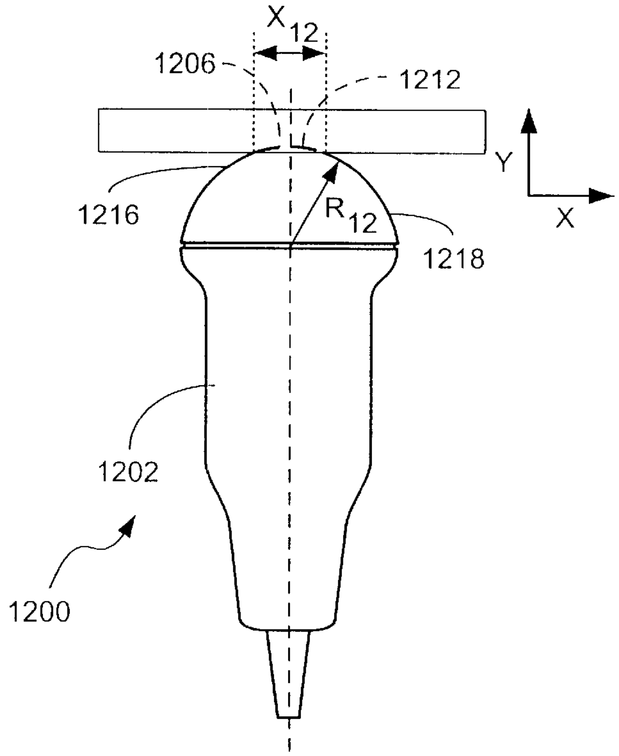
FIG. 12 is a plan view of an alternative embodiment of the present invention.
Figure 13:
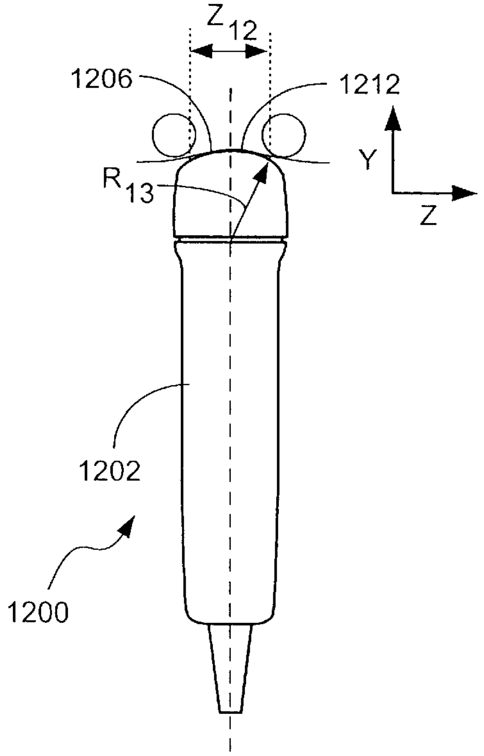
FIG. 13 is a side view of the embodiment of FIG. 12.

In FIGS. 12 and 13, an alternative embodiment of the transducer (transducer 1200) is depicted as including a body 1202 and a lens 1206. Lens 1206 is configured as an acoustically non-focusing lens. Lens 1206 is configured, such as by being formed of a selected material(s) and/or possessing a particular shape to propagate acoustic energy into a body, e.g., a human body, so that the acoustic energy does not tend to substantially focus within the body unless electronically focused. Lens 1206 preferably is formed, at least partially, of an acoustic-matching material. Preferably, lens 1206 incorporates a compound, generally spherically-shaped, tissue-engagement surface 1212. More specifically, the tissue-engagement surface 1212 is characterized by a first radius of curvature as viewed (in plan) in FIG. 12 and a second radius of curvature as viewed (in cross-section) in FIG. 13. Preferably, the first radius of curvature $R_{12}$ of the tissue-engagement surface is selected so as to provide an appropriate cross-sectional area of engagement for propagating acoustic energy from the transducer to a body. As depicted in FIG. 13, the second radius of curvature $R_{13}$ of tissue engagement surface 1212 also is selected so as to facilitate propagation of acoustic energy; however, the second radius also may be selected to exploit an appropriately selected acoustic window, such as by permitting acoustic access between adjacently spaced ribs, for example.

Surfaces 1216 and 1218 emanating from the tissue-engagement surface 1212 generally are curved and smooth surfaces that extend outwardly and rearwardly toward the transducer body. As viewed in plan (FIG. 12), surfaces 1216 and 1218 are characterized by substantially the same radius of curvature, e.g., $R_{12}$, so as to present an overall spherically-shaped exterior surface of the lens, as viewed in plan.

Figure 14:
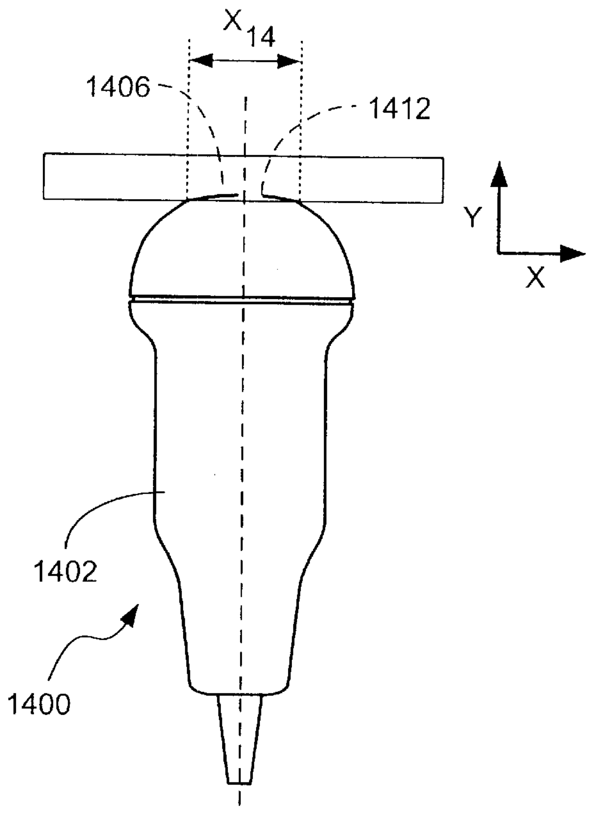
FIG. 14 is a plan view of an alternative embodiment of the present invention.
Figure 15:
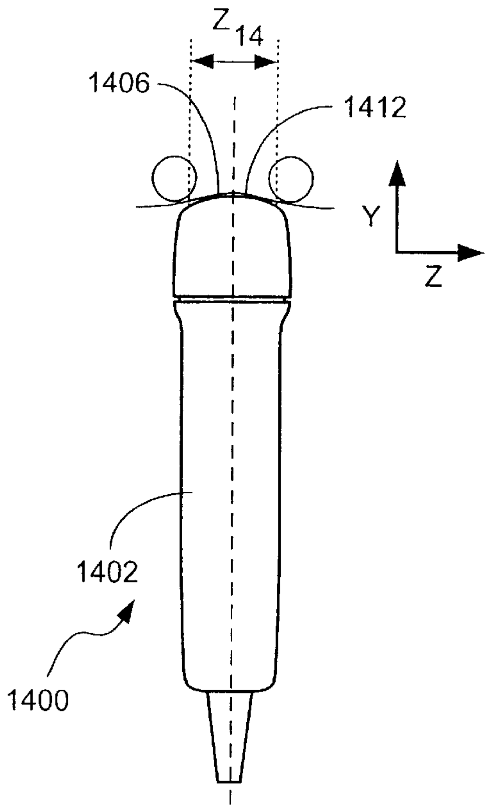
FIG. 15 is a side view of the embodiment of FIG. 14.

In FIGS. 14 and 15, an alternative embodiment of the transducer (transducer 1200) is depicted as including a body 1402 and a lens 1406. Lens 1406 is configured as an acoustically non-focusing lens. Lens 1406 is configured, such as by being formed of a selected material(s) and/or possessing a particular shape to propagate acoustic energy into a body, e.g., a human body, so that the acoustic energy does not tend to substantially converge or focus within the body unless electronically focused. Lens 1406 preferably is formed, at least partially, of an acoustic-matching material. Preferably, lens 1406 incorporates a compound, generally spherically-shaped, tissue-engagement surface 1412. More specifically, the tissue-engagement surface 1412 is characterized by first and second radii of curvature as viewed (in plan) in FIG. 14 and third and fourth radii of curvature as viewed (in cross-section) in FIG. 15.

Figure 16:
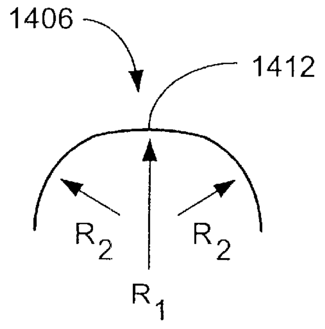
FIG. 16 is a schematic diagram depicting manufacturing detail of the lens of FIG. 14.
Figure 17:
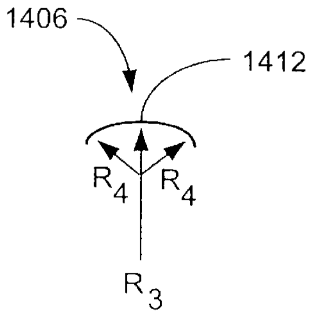
FIG. 17 is a schematic diagram depicting manufacturing detail of the lens of FIG. 15.

As shown in greater detail in FIGS. 16 and 17, the compound geometric structure of the embodiment depicted in FIGS. 14 and 15 clearly is evident. More specifically, as shown in FIG. 16, the lens includes a tissue-engagement surface that primarily is defined by a radius $R_1$ (in plan view). The surface defined by radius of curvature $R_1$ transitions at each of its ends to surfaces defined by radii of curvature $R_2$. Preferably, radii $R_2$ are defined by lengths that are shorter than the length of radius $R_1$. Similarly, when viewed from the side (FIG. 17), tissue-engagement surface also primarily is defined by a radius of curvature $R_3$. Each end of the tissue-engagement surface transitions to be defined by a radius of curvature $R_4$ that is shorter than radius $R_3$. So provided, the tissue-engagement surface presents a relatively flattened surface, as compared to the surfaces of the lens bounding the tissue-engagement area. Thus, the tissue-engagement surface may be viewed as providing a near optimal propagation medium while, advantageously, attempting to exploit the geometry-limited rib access points, among others.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention.

For example, although the invention has been described herein in relation to an ultrasonic imaging system for use in medical applications, such as with a patient, such systems may be utilized in various other applications as well. Additionally, various surfaces associated with the lens have been described herein as enabling convenient positioning of a transducer relative to an acoustic window. In other embodiments, one or more of these surface may be formed as a portion of the transducer body, such as on the nose of the transducer, to provide similar functionality. All such modifications and variations are intended to be included herein within the scope of this disclosure and the present invention and protected by the following claims.

What is claimed is:

1. An acoustic imaging system comprising:

a transducer lens configured to mate with a transducer body, said transducer lens being formed, at least partially, of an acoustic-matching material, said acoustic-matching material exhibiting acoustic properties substantially corresponding to acoustic properties of a body to be imaged such that acoustic energy transmitted from said transducer lens and into the body is substantially mechanically non-focused by said transducer lens.

2. The acoustic imaging system of claim 1, wherein said transducer lens has an acoustic velocity within the range of approximately 1.4 to approximately 1.6 mm/μsec.

3. The acoustic imaging system of claim 1, wherein said transducer lens has an acoustic impedance of between approximately 1.3 and 1.7 MRayl.

4. The acoustic imaging system of claim 1, wherein said transducer lens has a transducer-engagement end and a tissue-engagement surface, said transducer-engagement end being configured to engage a transducer body, said tissue engagement surface being formed as a substantially planar area.

5. The acoustic imaging system of claim 1, wherein said transducer lens has a transducer-engagement end and a tissue-engagement surface, said transducer-engagement end being configured to engage a transducer body, said tissue engagement surface being formed as a substantially cylindrically-shaped area.

6. The acoustic imaging system of claim 1, wherein said transducer lens has a transducer-engagement end and a tissue-engagement surface, said transducer-engagement end being configured to engage a transducer body, said tissue engagement surface being formed as a substantially spherically-shaped area.

7. The acoustic imaging system of claim 1, further comprising:

a transducer having a transducer body and an acoustic array, said transducer body mounting said acoustic array, said transducer lens being configured to engage said transducer body such that said acoustic array is encased by said transducer lens and said transducer body.

8. The acoustic imaging system of claim 1, further comprising:

means for propagating acoustic waves from said transducer lens.

9. The acoustic imaging system of claim 1, wherein said acoustical-matching material is selected from at least one of the group consisting of butadiene and styrene butadiene.

10. The acoustic imaging system of claim 7, further comprising:

an image processing system electrically communicating with said transducer, said image processing system being configured to provide signals to said transducer such that said acoustic array generates acoustic energy and transmits said acoustic energy through said transducer lens, thereby propagating acoustic waves from said transducer lens.

11. The acoustic imaging system of claim 8, wherein said means for propagating acoustic waves comprises:

means for accessing an acoustic window formed between adjacently disposed ribs of a patient.

12. The acoustic imaging system of claim 10, wherein said image processing system is configured to electronically focus said acoustic waves propagated from said transducer lens.

13. A method for acoustically imaging a body of a patient comprising the steps of:

providing a transducer having a transducer lens, the transducer lens being formed, at least partially of, an acoustic-matching material, said acoustic-matching material exhibiting acoustic properties substantially corresponding to acoustic properties of the body being imaged; and propagating acoustic waves from the transducer lens such that acoustic energy transmitted from said transducer lens and into the body is substantially mechanically non-focused by said transducer lens.

14. The method of claim 13, wherein the step of propagating acoustic waves comprises the steps of:

providing a signal to the transducer such that the transducer generates acoustic energy;

transmitting the acoustic energy through the transducer lens;

receiving reflected acoustic energy with the transducer; and processing the reflected acoustic energy to form an image.

15. The method of claim 13, wherein the step of providing a transducer comprises the step of:

providing a transducer lens formed, at least partially of, an acoustic-matching material selected from the group consisting of butadiene and styrene butadiene.

16. The method of claim 13, wherein the step of providing a transducer comprises the step of:

providing a transducer lens formed, at least partially of, an acoustic-matching material such that the transducer lens has an acoustic velocity within the range of approximately 1.4 to approximately 1.6 mm/μsec.

17. The method of claim 13, wherein the step of providing a transducer comprises the step of:

providing a transducer lens formed, at least partially of, an acoustic-matching material such that the transducer lens has an acoustic impedance of between approximately 1.3 and 1.7 MRayl.

18. The method of claim 13, wherein the step of providing a transducer comprises the step of:

providing a transducer lens having a transducer-engagement end and a tissue-engagement surface, the transducer-engagement end being configured to engage a transducer body, the tissue engagement surface being configured as one of the group consisting of: a substantially planar area, a substantially cylindrically-shaped area, and a substantially spherically-shaped area.

19. The method of claim 14, wherein the step of transmitting the acoustic energy comprises the steps of:

accessing an acoustic window formed between adjacently disposed ribs of a patient; and transmitting acoustic energy through the transducer lens and into the patient via the acoustic widow.

20. The method of claim 14, wherein the step of transmitting the acoustic energy comprises the steps of:

electronically focusing the acoustic energy in an elevational dimension; and electronically focusing the acoustic energy in a lateral dimension.

* * * * *